(12) United States Patent
Yildirim

(10) Patent No.: US 11,633,106 B2
(45) Date of Patent: Apr. 25, 2023

(54) SYSTEM AND METHOD FOR CHANGING A COSMETIC FORMULATION ATTRIBUTE

(71) Applicant: L'OREAL, Paris (FR)

(72) Inventor: Ozgur Emek Yildirim, Bellevue, WA (US)

(73) Assignee: L'OREAL, Paris (FR)

( * ) Notice: Subject to any disclaimer, the term of this patent is extended or adjusted under 35 U.S.C. 154(b) by 853 days.

(21) Appl. No.: 16/663,133

(22) Filed: Oct. 24, 2019

(65) Prior Publication Data
US 2021/0120936 A1 Apr. 29, 2021

(51) Int. Cl.
| A45D 33/02 | (2006.01) |
| A61B 5/00 | (2006.01) |
| B01J 19/12 | (2006.01) |
| B01J 19/08 | (2006.01) |

(52) U.S. Cl.
CPC ........... *A61B 5/0077* (2013.01); *B01J 19/088* (2013.01); *B01J 19/123* (2013.01); *A45D 2200/205* (2013.01)

(58) Field of Classification Search
CPC ........ A45D 2044/007; A45D 2200/205; A45D 44/005; A45D 44/22; A61B 5/0077; Y02T 10/40; B01J 19/088; B01J 19/123
See application file for complete search history.

(56) References Cited

U.S. PATENT DOCUMENTS

| 5,858,381 A | 1/1999 | Le Bras et al. |
| 6,120,781 A | 9/2000 | Le Bras et al. |
| 6,960,339 B1 | 11/2005 | Ferrari |
| 7,144,582 B1 | 12/2006 | Ferrari et al. |
| 2001/0051171 A1 | 12/2001 | Mondet |

(Continued)

FOREIGN PATENT DOCUMENTS

| EP | 1068856 A1 | 1/2001 |
| EP | 1249223 A1 | 10/2002 |

(Continued)

OTHER PUBLICATIONS

FR2933585A1 Google translation (Year: 2010).*

(Continued)

*Primary Examiner* — Ellen M McAvoy
*Assistant Examiner* — Chantel L Graham
(74) *Attorney, Agent, or Firm* — Christenson O'Connor Johnson Kindness PLLC

(57) ABSTRACT

Systems and methods for changing a cosmetic formulation attribute are described. In an embodiment, the system comprises a detector configured to detect a cosmetic formulation disposed on the substrate; an additive applicator configured to apply an additive to the cosmetic formulation disposed on the substrate, wherein the additive is configured to change a cosmetic formulation attribute; and a controller operatively coupled to the detector and the additive applicator. In an embodiment, controller includes logic that, when executed by the controller, is configured to cause the system to perform operations including: detecting, with the detector, the cosmetic formulation disposed on the substrate; and applying, with the additive applicator, the additive to the cosmetic formulation disposed on the substrate to change the cosmetic formulation attribute of the cosmetic formulation.

17 Claims, 5 Drawing Sheets

(56) References Cited

U.S. PATENT DOCUMENTS

| | | | |
|---|---|---|---|
| 2001/0053377 A1 | 12/2001 | Mondet et al. | |
| 2003/0017124 A1 | 1/2003 | Agostini et al. | |
| 2003/0068348 A1 | 4/2003 | Ferrari et al. | |
| 2008/0014232 A1 | 1/2008 | Arnaud et al. | |
| 2010/0266647 A1 | 10/2010 | Dingley et al. | |
| 2012/0312316 A1 | 12/2012 | Tomita et al. | |

FOREIGN PATENT DOCUMENTS

| | | | | |
|---|---|---|---|---|
| EP | 1332753 A2 | 8/2003 | | |
| EP | 1502574 A1 | 2/2005 | | |
| EP | 1555009 A1 | 7/2005 | | |
| FR | 2933585 A1 * | 1/2010 | ........... | A45D 44/005 |
| FR | 2933585 A1 | 1/2010 | | |
| WO | 2003/039293 A1 | 5/2003 | | |
| WO | 2007/022095 A1 | 2/2007 | | |
| WO | 2016/014889 A1 | 1/2016 | | |

OTHER PUBLICATIONS

International Preliminary Report on Patentability and Written Opinion dated Apr. 26, 2022, for International Patent Application No. PCT/US2020/056514, filed Oct. 20, 2020, 8 pages.
International Search Report and Written Opinion dated Feb. 2, 2021, for International Patent Application No. PCT/US2020/056514, filed Oct. 20, 2020, 13 pages.

* cited by examiner

SYSTEM AND METHOD FOR CHANGING A COSMETIC FORMULATION ATTRIBUTE

SUMMARY

In an aspect, the present disclosure provides a system for changing a cosmetic formulation attribute of a cosmetic formulation disposed on a substrate. In an embodiment, the system generally includes a detector configured to detect a cosmetic formulation disposed on the substrate; an additive applicator configured to apply an additive to the cosmetic formulation disposed on the substrate, wherein the additive is configured to change a cosmetic formulation attribute; and a controller operatively coupled to the detector and the additive applicator, wherein the controller includes logic that, when executed by the controller, is configured to cause the system to perform operations including: detecting, with the detector, the cosmetic formulation disposed on the substrate; and applying, with the additive applicator, the additive to the cosmetic formulation disposed on the substrate to change the cosmetic formulation attribute of the cosmetic formulation.

In another aspect, the present disclosure provides a method of changing an attribute of a cosmetic formulation disposed on a substrate. In an embodiment, the method generally includes detecting, with a detector, the cosmetic formulation disposed on the substrate; applying, with an additive applicator, the additive to the cosmetic formulation disposed on the substrate to change the cosmetic formulation attribute of the cosmetic formulation.

In accordance with any of the embodiments disclosed herein, the cosmetic formulation includes a polymer configured to crosslink upon exposure to the additive, thereby contracting the cosmetic formulation. In accordance with any of the embodiments disclosed herein, the additive includes electromagnetic radiation, wherein the additive applicator includes a light source configured to apply the electromagnetic radiation to the cosmetic formulation disposed on the substrate, and wherein the operations further include applying, with the additive applicator, the electromagnetic radiation to the cosmetic formulation for a duration and at an intensity sufficient to crosslink the polymer in the cosmetic formulation. In accordance with any of the embodiments disclosed herein, the polymer is a component of a thermoset configured to crosslink upon exposure to heat, wherein the additive applicator is configured to apply heat to the cosmetic formulation disposed on the substrate for a time and at a temperature sufficient to crosslink the thermoset. In accordance with any of the embodiments disclosed herein, the additive applicator is configured to generate a plasma and apply the plasma to the cosmetic formulation disposed on the substrate, wherein the polymer is configured to crosslink upon exposure to the plasma. In accordance with any of the embodiments disclosed herein, the additive applicator is configured to apply an additive selected from a crosslinker and an initiator to the cosmetic formulation disposed on the substrate, wherein, prior to application of the additive, the cosmetic formulation does not include a crosslinking component selected from a crosslinker and an initiator.

In accordance with any of the embodiments disclosed herein, the cosmetic formulation includes a water-swellable polymer configured to expand upon exposure to water, wherein the additive applicator is configured to apply water to the cosmetic formulation disposed on the substrate, thereby swelling the cosmetic formulation.

In accordance with any of the embodiments disclosed herein, the system generally includes a user input configured to receive input from a user to define, at least in part, the cosmetic formulation attribute. In accordance with any of the embodiments disclosed herein, the user input is operatively coupled to the controller, and wherein the controller further includes logic that, when executed by the controller, is configured to cause the system to perform operations including applying the additive to at least a portion of the cosmetic formulation disposed on the substrate based upon the cosmetic formulation attribute. In accordance with any of the embodiments disclosed herein, the controller further includes logic that, when executed by the controller, is configured to cause the system to perform operations including detecting, with the detector, a feature of the substrate; and applying the additive to at least a portion of the cosmetic formulation disposed on the substrate based upon the cosmetic formulation attribute and the feature of the substrate.

In accordance with any of the embodiments disclosed herein, the system generally includes a cosmetic formulation applicator configured to apply the cosmetic formulation to at least a portion of the substrate. In accordance with any of the embodiments disclosed herein, the cosmetic formulation applicator is operatively coupled to the controller, and wherein the controller further includes logic that, when executed by the controller, is configured to cause the system to perform operations including applying the cosmetic formulation to the substrate based upon the cosmetic formulation attribute.

In accordance with any of the embodiments disclosed herein, the substrate is chosen from a finger nail, skin, hair, and combinations thereof. In accordance with any of the embodiments disclosed herein, the cosmetic formulation is chosen from a lotion, a hair dye, a foundation, a blush, a rouge, a lipstick, a lip gloss, a nail polish, and a nail varnish.

This foregoing summary is provided to introduce a selection of concepts in a simplified form that are further described below in the Detailed Description. This summary is not intended to identify key features of the claimed subject matter, nor is it intended to be used as an aid in determining the scope of the claimed subject matter.

DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein.

The detailed description set forth below in connection with the appended drawings, where like numerals reference like elements, is intended as a description of various embodiments of the disclosed subject matter and is not intended to represent the only embodiments. Each embodiment described in this disclosure is provided merely as an example or illustration and should not be construed as preferred or advantageous over other embodiments. The illustrative examples provided herein are not intended to be exhaustive or to limit the claimed subject matter to the precise forms disclosed.

DETAILED DESCRIPTION

Described herein are systems and methods for changing a cosmetic formulation attribute. Conventionally, cosmetic formulations are applied to substrates, such as portions of skin, finger nails, and the like, without the ability to change an attribute of the applied cosmetic formulation, such as a topography, texture, sheen, or shape of the cosmetic formulation. It would be advantageous if attributes of a cosmetic formulation could be changed or altered once applied to a substrate. Particularly, it would be advantageous if an attribute of a portion of the cosmetic formulation could be altered in a targeted or systematic fashion to provide a desired topography, shape, sheen, or texture on the substrate.

Toward that end, the present disclosure provides systems and methods for changing a cosmetic formulation attribute of a cosmetic formulation disposed on a substrate. In an embodiment, the system generally includes a detector configured to detect a cosmetic formulation disposed on the substrate; an additive applicator configured to apply an additive to the cosmetic formulation disposed on the substrate, wherein the additive is configured to change a cosmetic formulation attribute; and a controller operatively coupled to the detector and the additive applicator. As will be described in more detail below, in an embodiment, the controller includes logic that, when executed by the controller, is configured to cause the system to perform operations including: detecting, with the detector, the cosmetic formulation disposed on the substrate; and applying, with the additive applicator, the additive to the cosmetic formulation disposed on the substrate to change the cosmetic formulation attribute of the cosmetic formulation.

In the following description, numerous specific details are set forth in order to provide a thorough understanding of one or more embodiments of the present disclosure. It will be apparent to one skilled in the art, however, that many embodiments of the present disclosure may be practiced without some or all of the specific details. Further, it will be appreciated that embodiments of the present disclosure may employ any combination of features described herein.

Systems

Figure 1A:
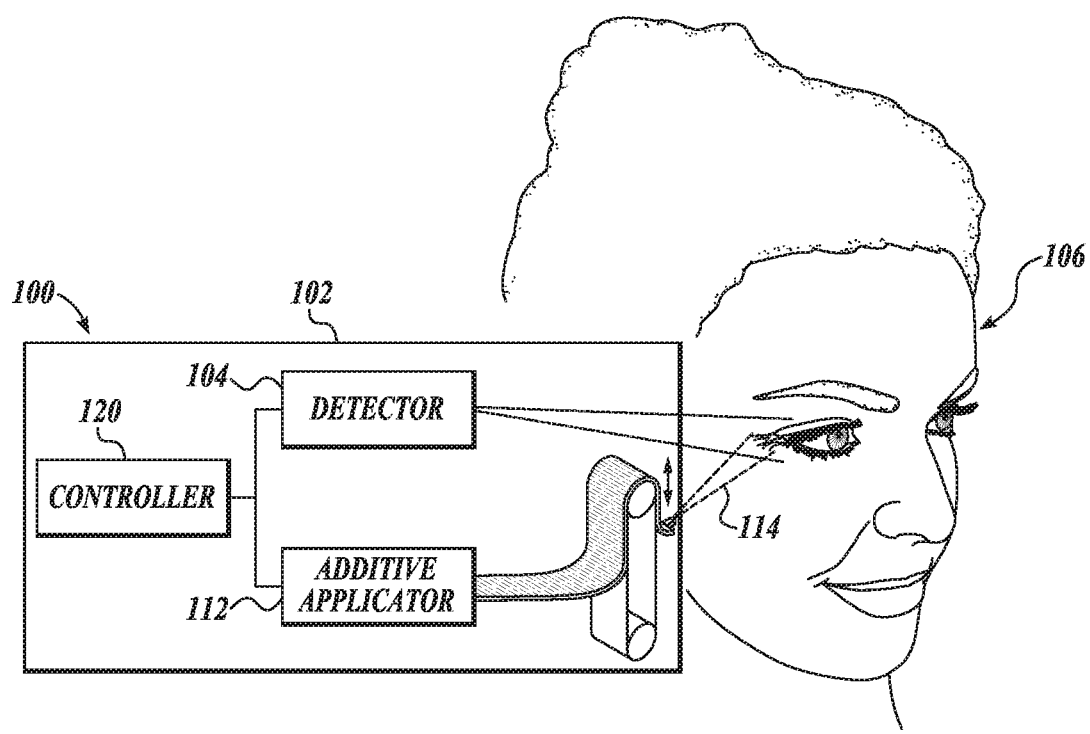
FIG. 1A schematically illustrates a system, in accordance with an embodiment of the disclosure, shown detecting a cosmetic formulation disposed on a substrate and applying an additive to the substrate.
Figure 1B:
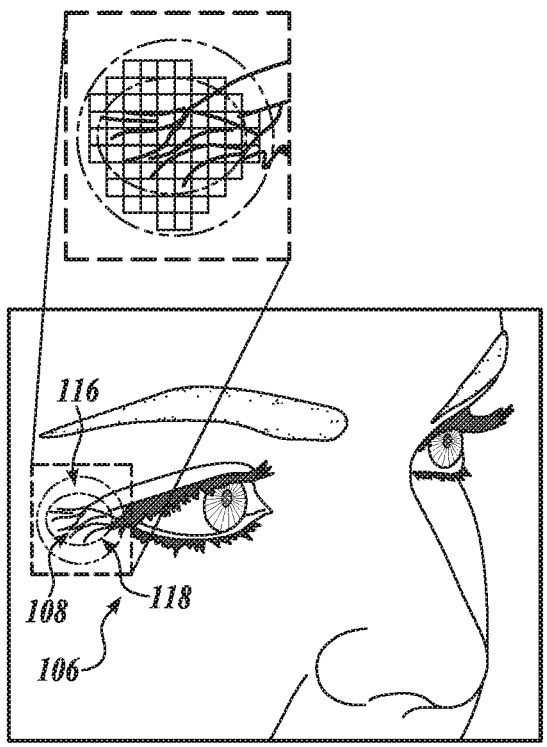
FIG. 1B is another illustration of the substrate of FIG. 1A, shown here as a portion of skin around an eye prior to application of the additive, and a magnified view of the portion of skin with pixels overlaying the portion of skin, in accordance with an embodiment of the disclosure.
Figure 1C:
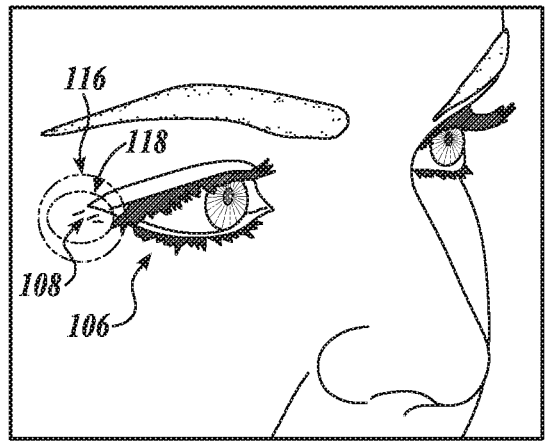
FIG. 1C is another illustration of the substrate of FIG. 1B after application of the additive to the substrate showing a change in an attribute of a cosmetic formulation disposed on the substrate, in accordance with an embodiment of the disclosure.

In an aspect, the present disclosure provides systems for changing a cosmetic formulation attribute of a cosmetic formulation disposed on a substrate. In this regard, attention is directed to FIGS. 1A-1C, in which a system 100, in accordance with an embodiment of the disclosure, is shown. FIG. 1A schematically illustrates the system 100, in accordance with an embodiment of the disclosure, shown detecting a cosmetic formulation 116 disposed on a substrate 106 and applying an additive 114 to cosmetic formulation 116 the substrate 106. FIG. 1B is an illustration of the substrate 106, shown here as a portion of skin around an eye, prior to application of the additive 114, and a magnified view of the portion of skin with pixels 110 overlaying the portion of skin, in accordance with an embodiment of the disclosure. FIG. 1C is an illustration of the substrate 106 of FIG. 1B after application of the additive 114 to the substrate 106, showing a change in an attribute of a cosmetic formulation 116 disposed on the substrate 106, in accordance with an embodiment of the disclosure.

In the illustrated embodiment, the system 100 is shown to include a detector 104 configured to detect a substrate 106, shown here as a portion of skin adjacent to an eye and cosmetic formulation 116 disposed thereon, an additive applicator 112 configured to apply the additive 114 to the cosmetic formulation 116 disposed on the substrate 106, and a controller 120 operatively coupled to the detector 104 and the additive applicator 112. As shown, the detector 104, additive applicator 112, and controller 120 are disposed within a housing 102. In an embodiment, the housing 102 is shaped to be held and manipulated by a hand, such as a hand of a user. In an embodiment, the housing 102 is shaped to be placed on a flat surface, such as a table top.

In an embodiment, the detector 104 is configured to detect a cosmetic formulation 116 disposed on the substrate 106. Such a detector 104 can include an optical detector 104 configured to detect light reflected, scattered, absorbed, emitted, and the like by a cosmetic formulation 116 disposed on the substrate 106. As discussed further herein, in an embodiment, the additive applicator 112 includes a light source configured to emit light onto the substrate 106. In an embodiment, the light detected by the detector 104 is light emitted from the additive applicator 112. While optical detectors are described herein, it will be understood that other types of detectors can be used in accordance with embodiments of the present disclosure. In an embodiment, detector 104 is an inertial sensor.

As above, in the illustrated embodiment, the controller 120 is operatively coupled to the detector 104. In this regard, the detector 104 and controller 120 are configured to exchange signals, such as signals based on, for example, the presence or absence of a cosmetic formulation 116 disposed on the substrate 106. Accordingly, in an embodiment, the controller 120 includes logic that, when executed by the controller 120, is configured to cause the system 100 to perform operations including detecting, with the detector 104, the cosmetic formulation 116 disposed on the substrate 106.

In an embodiment, signals exchanged between the detector 104 and the controller 120 are suitable to define whether and where an additive 114 is applied to a cosmetic formulation 116 disposed on the substrate 106. In an embodiment, the controller 120 includes logic that, when executed by the controller 120, is configured to cause the system 100 to perform operations including applying, with the additive applicator 112, the additive 114 to all or a portion of the cosmetic formulation 116 disposed on the substrate 106 to change a cosmetic formulation attribute of the cosmetic formulation 116, such as based on signals from the detector 104. In this regard, the system 100 is configured selectively deposit the additive 114 to portions of the substrate 106, such as those including the cosmetic formulation 116 disposed thereon. In the illustrated embodiment, the additive applicator 112 includes a gantry configured to move an application portion of the additive applicator 112 relative to the substrate 106 to selectively apply the additive 114 to one or more portions of the substrate 106.

In an embodiment, a user may guide the system 100 on where to apply the additive 114. In an embodiment, a user may define a portion of the substrate 106 to be contacted by the additive 114 by applying the cosmetic formulation 116 to the substrate 106. Accordingly, in an embodiment, the system 100 applies the additive 114 to the cosmetic formulation 116 disposed on the substrate 100, which the user applied. In an embodiment, a user may define a portion of the substrate 106 to be contacted by the additive 114 by applying a marker to the portion of the substrate 106. In an embodiment, the system 100 is configured to apply the additive 114 to those portions of the substrate 106 on which the marker is disposed, such as by detecting the marker with the detector 104. In this regard, the system 100 is configured to make guided or supervised decisions on whether and where to apply the additive 114 to the substrate 106. In an embodiment, the marker includes a substance, such as a dye or other colored material, such as a substance disposed in a pen or other marker applicator.

In an embodiment, the system 100 is configured to detect a feature 108 of the substrate 106 and selectively apply to the additive 114 to a portion of the substrate 106 including the feature 108 based, in part, on the detected feature 108 of the substrate 106. As shown in FIG. 1B, the substrate 106 includes a portion of skin adjacent to any eye. The portion of skin is shown to include a number of wrinkles 108 and a portion 118 of the cosmetic formulation 116 disposed on the wrinkles 108, as well as other portions of the skin. The magnified portion of FIG. 1B is overlaid with a number of pixels 110, such as pixels 110 defined and detected by the detector 104. As shown, the pixels 110 include pixels 110 overlaid on the wrinkles 108, as well as those over portions of the substrate 106 that do not include wrinkles 108. In an embodiment, the additive applicator 112 applies additive 114 to portion 118 of the cosmetic formulation 116 disposed on the feature 108, such as detected in pixels 110 overlaid on the substrate 106 that include wrinkles 108. In an embodiment, the additive applicator 112 is configured to apply additive 114 to portions of skin including the detected feature 108 and in response to signals generated by the detector 104, such as by rastering the additive applicator 112 over the portion of skin and applying the additive 114 to portions of the substrate 106 corresponding to the pixels 110 that include the detected feature 108. In this regard, the additive 114 is applied to the portions of the substrate 106 including the detected feature 108, such as in registry with pixels 110 containing the cosmetic formulation 116 disposed over the detected feature 108.

In this regard, the system 100 is configured to selectively contact the cosmetic formulation 116 disposed on portions of the substrate 106 that include the detected feature 108 with the additive 114 to change an attribute of the contacted cosmetic formulation 116. As shown in FIG. 1C, the wrinkles 108 contacted by the additive 114 are generally reduced, thereby changing an attribute of the cosmetic formulation 116, and, in turn, an appearance of the feature 108 of the substrate 106.

Figure 2A:
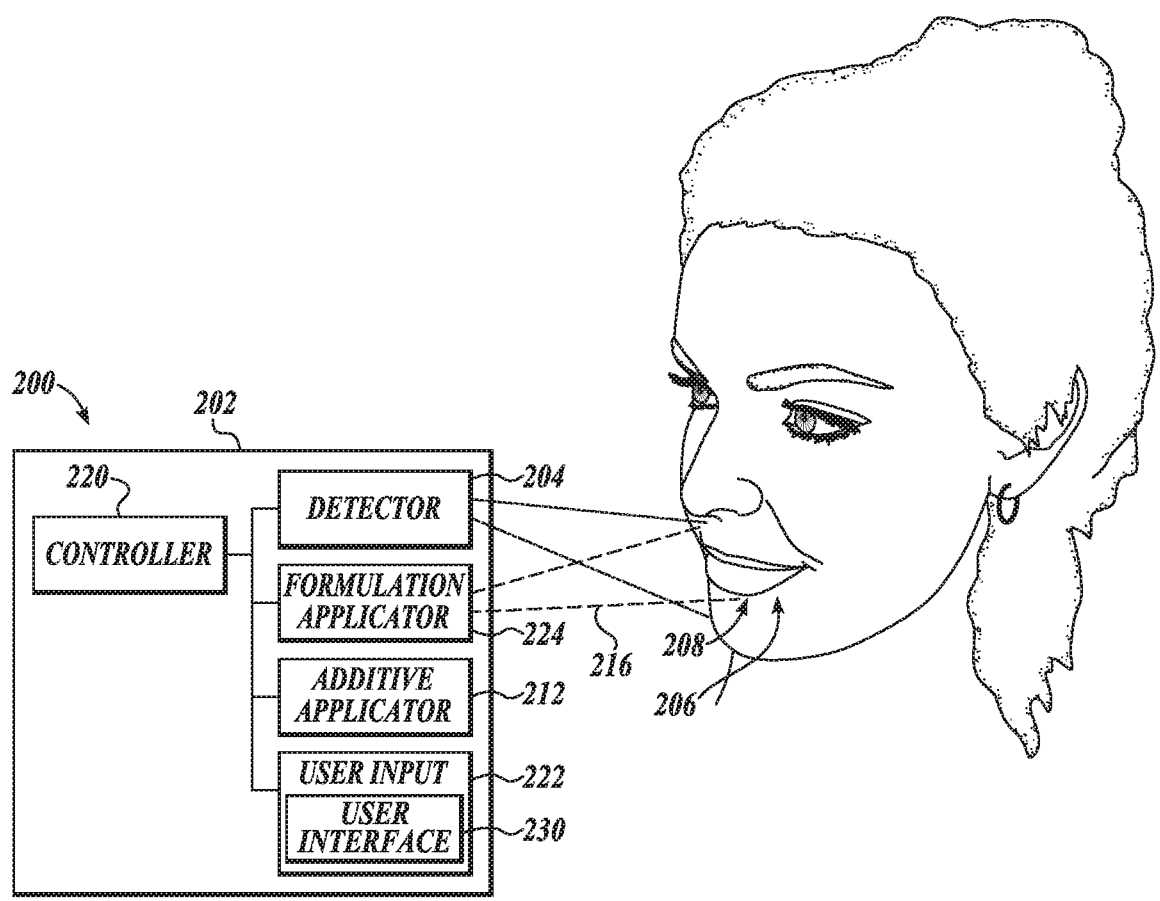
FIG. 2A is a schematic illustration of another system, in accordance with an embodiment of the disclosure, shown detecting a feature of a substrate and applying a cosmetic formulation to a portion of the substrate including the feature.
Figure 2B:
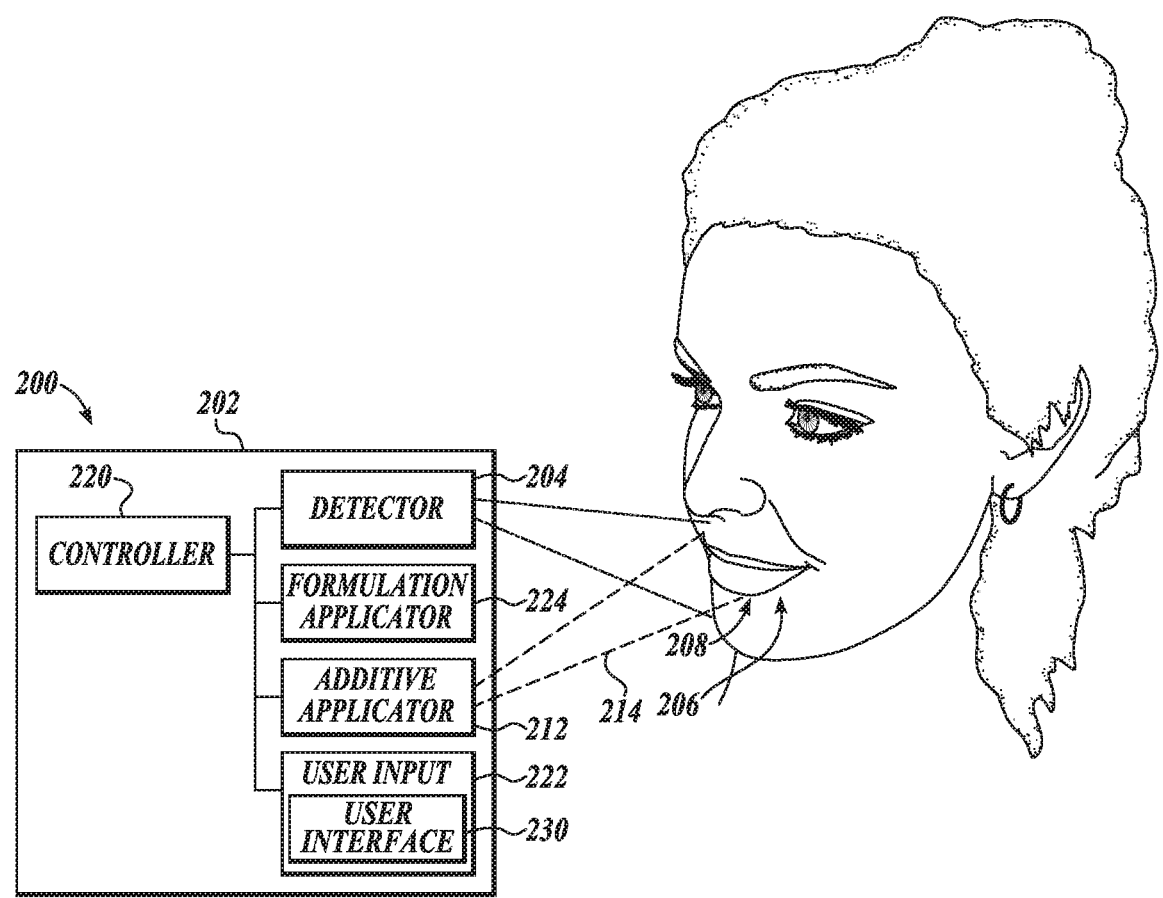
FIG. 2B is another illustration of the system of FIG. 2A, shown detecting the cosmetic formulation applied to the substrate and applying an additive to the cosmetic formulation, in accordance with an embodiment of the disclosure.
Figure 2C:
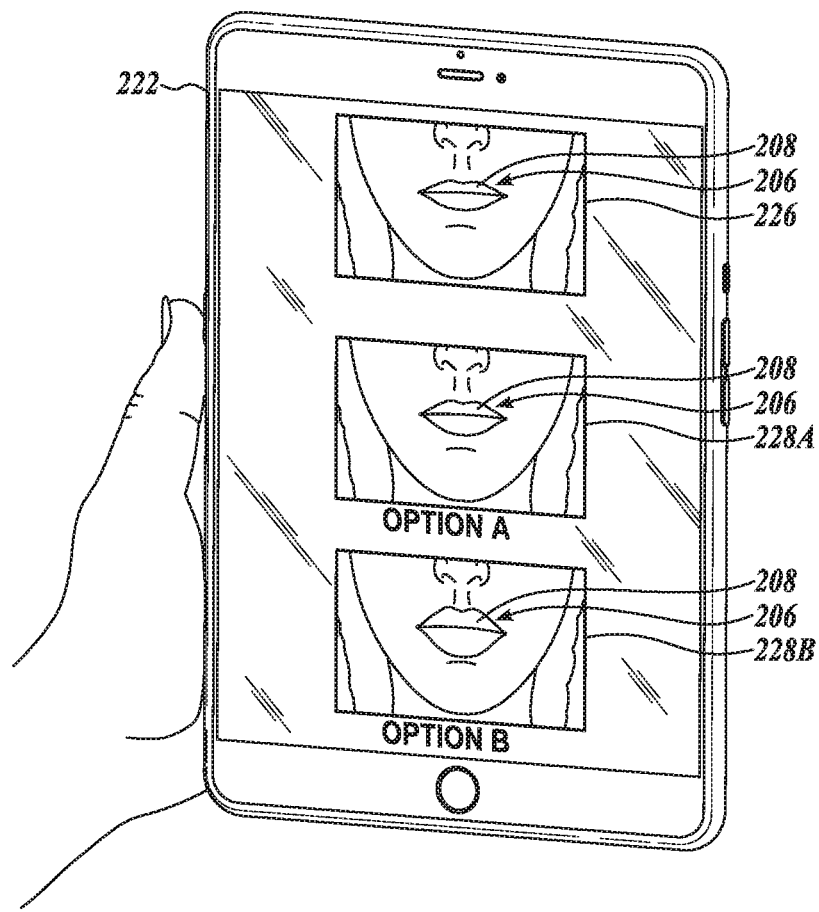
FIG. 2C is an illustration of a user input of the system of FIG. 2A, in accordance with an embodiment of the disclosure.

The substrate 106 can include any substrate onto which cosmetic formulations are applied. As shown in FIGS. 1A-1C, the substrate 106 can include a portion of skin, such as a portion of skin adjacent to an eye. As shown in FIGS. 2A-2C, the substrate 206 can further include lips. In an embodiment, the substrate 106 is chosen from a finger nail, skin, hair, and combinations thereof. In an embodiment, the cosmetic formulation 116 is chosen from a lotion, a hair dye, a foundation, a blush, a rouge, a lipstick, a lip gloss, a nail polish, and a nail varnish.

In an embodiment, the cosmetic formulation 116 includes a polymer configured to crosslink upon exposure to the additive 114. Accordingly, in an embodiment, the cosmetic formulation 116 is configured to contract upon exposure to the additive 114. Such contraction of the cosmetic formulation 116 can generate tension in, for example, the cosmetic formulation 116 disposed on skin, thereby reducing a number of or smoothing wrinkles 108 on the skin. As illustrated in FIG. 1B the portion of skin has wrinkles 108 prior to application of the additive 114, whereas the wrinkles 108 are reduced after application of the additive 114, as shown in FIG. 1C.

In an embodiment, the system 100 includes the cosmetic formulation 116, configured to react with or otherwise change an attribute of the cosmetic formulation 116 when contacted with the additive 114. In an embodiment, the cosmetic formulation 116 is integrated within the system 100, as discussed further herein with respect to the FIGS. 2A-2C. In an embodiment, the cosmetic formulation 116 is sold or packaged with other components of the system 100. In an embodiment, the cosmetic formulation 116 is sold separately from the system 100.

In an embodiment, the cosmetic formulation 116 includes a polymer configured to crosslink upon exposure to electromagnetic radiation. In this regard, the additive 114 includes electromagnetic radiation and the additive applicator 112 includes one or more light sources. Such electromagnetic radiation can initiate a crosslinking reaction between the polymer and a crosslinker, also present in the cosmetic formulation 116. In an embodiment, the controller 120 includes logic that, when executed by the controller 120, is configured to cause the system 100 to perform operations including applying, with the additive applicator 112, the electromagnetic radiation to the cosmetic formulation 116 for a duration and at an intensity sufficient to crosslink the polymer in the cosmetic formulation 116.

In an embodiment, the electromagnetic radiation emitted by the additive applicator 112 includes light in one or more wavelength ranges configured to crosslink the polymer of the cosmetic formulation 116. Such electromagnetic radiation can include, for example, ultraviolet light, such as light having wavelengths in a range of about 10 nm to about 400 nm, visible light, such a light having wavelengths in a range of about 400 nm to about 700 nm, and infrared light, such as light having wavelengths in a range of about 700 nm to about 1 mm.

In an embodiment, the additive applicator 112 is configured to apply heat to the substrate 106, such as where a cosmetic formulation 116 is configured to crosslink and contract upon exposure to heat. Such a cosmetic formulation 116 can include, for example, a cosmetic formulation 116 comprising one or more components of a thermoset, configured to crosslink upon exposure to heat. In an embodiment, the additive applicator 112 is configured to apply heat to the cosmetic formulation 116 disposed on the substrate 106 for a time and at a temperature sufficient to crosslink the thermoset.

In an embodiment, the additive applicator 112 includes a plasma generator configured to generate a plasma, such as a monomer plasma, and apply the plasma to the cosmetic formulation 116 disposed on the substrate 106, such as where the polymer of the cosmetic formulation 116 is configured to crosslink upon exposure to the plasma. Such plasma-based crosslinking can be beneficial where gradations in changing an attribute of the cosmetic formulation 116 are desirable, since the plasma tends to diffuse once emitted by the additive applicator 112. Plasma-based crosslinking is in contrast to certain embodiments of light-based crosslinking, which provides a more targeted application of the additive 114 to a cosmetic formulation 116 disposed on a substrate 106.

In an embodiment, the additive applicator 112 is configured to apply an additive 114 selected from a crosslinker and an initiator to the cosmetic formulation 116 disposed on the substrate 106. Such an additive applicator 112 can include an additive applicator 112 configured to apply selectively droplets comprising one or both of the crosslinker and the initiator to the cosmetic formulation 116 disposed on the substrate 106, for example based upon cosmetic formulation 116 disposed on the substrate 106 detected by the detector 104. In an embodiment, the additive applicator 112 includes an inkjet printer, such as a thermal or piezoelectric ink jet printer, configured to eject droplets comprising the additive 114 onto the cosmetic formulation 116 disposed on the substrate 106.

In an embodiment, the systems of the present disclosure include a user input configured to receive input from a user to define, at least in part, a cosmetic formulation attribute to be changed by the system. In this regard, attention is directed to FIGS. 2A-2C, in which a system 200 in accordance with an embodiment of the disclosure is illustrated. In the illustrated embodiment, the system 200 is shown to include a detector 204 configured to detect a cosmetic formulation 216 disposed on the substrate 206; an additive applicator 212 configured to apply an additive 214 to the cosmetic formulation 216 disposed on the substrate 206; a cosmetic formulation 216 applicator configured to apply the cosmetic formulation 216 to at least a portion of the substrate 206; a user input 222 including a user interface 230 configured to receive input from a user; and a controller 220 operatively coupled to the detector 204, the formulation applicator, the additive applicator 212, and the user input 222.

As above, in an embodiment, the user input 222 is configured to receive input from a user to define, at least in part, the cosmetic formulation attribute. In this regard, a user can define for themselves a cosmetic formulation attribute, such as from a list or other organization of possible or suggested cosmetic formulation attributes or as a custom cosmetic formulation attribute based upon their input. FIG. 2C is an illustration of a user input 222 of the system 200 of FIG. 2A, in accordance with an embodiment of the disclosure. In the illustrated embodiment, the user input 222, shown as a tablet, displays an image 226 of a substrate 206, shown here as lips, a first cosmetic formulation attribute design 228A of the substrate 206, and a second cosmetic formulation attribute design 228B. As shown, the first and second cosmetic formulation attribute designs 228A and 228B show the lips having varying degrees of plumpness. A user can select with the user input 222 one or more cosmetic formulation attribute designs using the user interface. While the illustrated user input 222 is shown to provide suggested cosmetic formulation attributes, in an embodiment, the user input 222 is configured to generate custom cosmetic formulation attributes based upon, for example, images of the substrate 206 generated by the detector 204 and input from a user. In this regard, in an embodiment, a user can draw or otherwise mark or modify the image 226 to indicate whether and where the cosmetic formulation 216 and the additive 214 are applied. Such guided or semi-guided application of the cosmetic formulation 216 and the additive 214 to the substrate 206 are suitable to generate custom or semi-custom cosmetic formulation attributes.

As shown in FIGS. 2A and 2B, the user input 222 is operatively coupled to the controller 220 and configured to exchange signals therebetween. As shown in FIG. 2C, in an embodiment, the user input 222 includes a personal computing device, such as a tablet, a phone, and the like, such as a personal computing device in wireless communication with one or more components of the system 200, such as the additive applicator 212 and the detector 204.

In the illustrated embodiment, the system 200 is shown to include a cosmetic formulation applicator 224 operatively coupled to the controller 220 and configured to apply the cosmetic formulation 216 to at least a portion of the substrate 206. As discussed further herein, the cosmetic formulation 216 is configured to react with or otherwise change an attribute of the cosmetic formulation 216 when contacted with the additive 214. In an embodiment, the cosmetic formulation 216 is configured to swell or expand when contacted by the additive 214, such as where the cosmetic formulation 216 comprises a water-swellable polymer. In an embodiment, the cosmetic formulation 216 is configured to contract when contacted by the additive 214, such as where the cosmetic formulation is configured to crosslink when contacted by the additive 214.

In an embodiment, the cosmetic formulation applicator 224 is configured to selectively apply the cosmetic formulation 216 to the substrate 206, such as through selective generation of one or more cosmetic formulation 216 droplets. As also shown in FIG. 2A, the detector 204 is configured to detect a feature 208 of the substrate 206, shown here as lips of a user. In an embodiment, the system 200 is configured to apply the formulation to the substrate 206 based upon a detected feature 208 of the substrate 206, such as a feature 208 of the substrate 206 detected with the detector 204. In this regard, in an embodiment the controller 220 further includes logic that, when executed by the controller 220, is configured to cause the system 200 to perform operations including: applying the cosmetic formulation 216 to the substrate 206 based upon the detected feature 208.

In an embodiment, the system 200 is configured to apply the cosmetic formulation 216 to the substrate 206 based upon input from the user, such as input received by the user input 222. Accordingly, in an embodiment the controller 220 further includes logic that, when executed by the controller 220, is configured to cause the system 200 to perform operations including: applying the cosmetic formulation 216 to the substrate 206 based upon a cosmetic formulation attribute, such as a cosmetic formulation attribute selected by user using the user input 222. In this regard, a user can select a portion of the substrate 206, shown here as lips, including a feature 208 on which to apply the cosmetic formulation 216. In response, the system 200 detects the portion of the substrate 206 including the feature 208 and then deposits the cosmetic formulation 216 onto that portion of the substrate 206.

In an embodiment, the controller 220 further includes logic that, when executed by the controller 220, is configured to cause the system 200 to perform operations including applying the additive 214 to at least a portion of the cosmetic formulation 216 disposed on the substrate 206 based upon the selected cosmetic formulation attribute(s). In this regard, the system 200 is configured to apply the additive 214 based, at least in part, upon the input from the user, and the cosmetic formulation attribute is customizable by the user.

As above, the user input 222 is illustrated to show an image of substrate 206 including lips 208 and different cosmetic formulation attribute designs 228A and 228B including lips 208 of varying degrees of plumpness. In an embodiment, the cosmetic formulation 216 includes a water-swellable polymer configured to expand upon exposure to water. In an embodiment, the additive 214 includes water. Such water, when applied by the additive applicator 212, is configured to swell the water-swellable polymer, thereby making, for example, the lips plumper and changing a cosmetic formulation attribute or cosmetic formulation 216. The water-swellable polymer can be swelled to varying degrees by applying more or less water with the additive applicator 212. Accordingly, in an embodiment, the system 200 is configured to apply an amount of water with the additive applicator 212 based upon an input from the user received by the user input 222, such as a selection between different cosmetic formulation attribute designs 228A and 228B.

In an embodiment, the additive 214 further comprises one or more components, such as components configured to crosslink the water-swellable polymer, suitable to cure or set the cosmetic formulation 216. In this regard, the additive is configured to both swell or plump the water-swellable polymer and cure or set the cosmetic formulation 216, such that the cosmetic formulation 216 does not continue to swell or plump in response to further exposure to water. Such components can include, for example, a crosslinker, an initiator, and the like, as discussed further herein with respect to FIGS. 1A-1C.

FIG. 2B is an illustration of the system 200 of FIG. 2A, shown detecting the cosmetic formulation 216 applied to the substrate 206 and applying the additive 214 to the cosmetic formulation 216, in accordance with an embodiment of the disclosure. In an embodiment, the system 200 is configured to apply the additive 214 to the cosmetic formulation 216 disposed on the substrate 206 based, at least in part, on the cosmetic formulation 216 detected by the detector 204. As discussed further herein with respect to FIGS. 1A-1C, in an embodiment, the controller 220 further includes logic that, when executed by the controller 220, is configured to cause the system 200 to perform operations including: detecting, with the detector 204, a feature 208 of the substrate 206; and applying the additive 214 to at least a portion of the cosmetic formulation 216 disposed on the substrate 206 based upon the cosmetic formulation attribute and the feature 208 of the substrate 206.

The system 200 of the present disclosure can take a number of form factors. In an embodiment, the system 200 is disposed in a housing 202, such as a housing 202 configured to sit on a table or benchtop. As above, in an embodiment, the system 200 can include a personal computing device, such as a handheld personal computing device. Accordingly, in an embodiment, one or more portions of the system 200 can be handheld and operate to detect a portion of the substrate 206. In an embodiment, the system 200 includes one or more components shaped to couple with the handheld computing device such that the additive 214 and/or the cosmetic formulation 216 can be applied while being held in a hand of, for example, a user.

Methods

Figure 3:
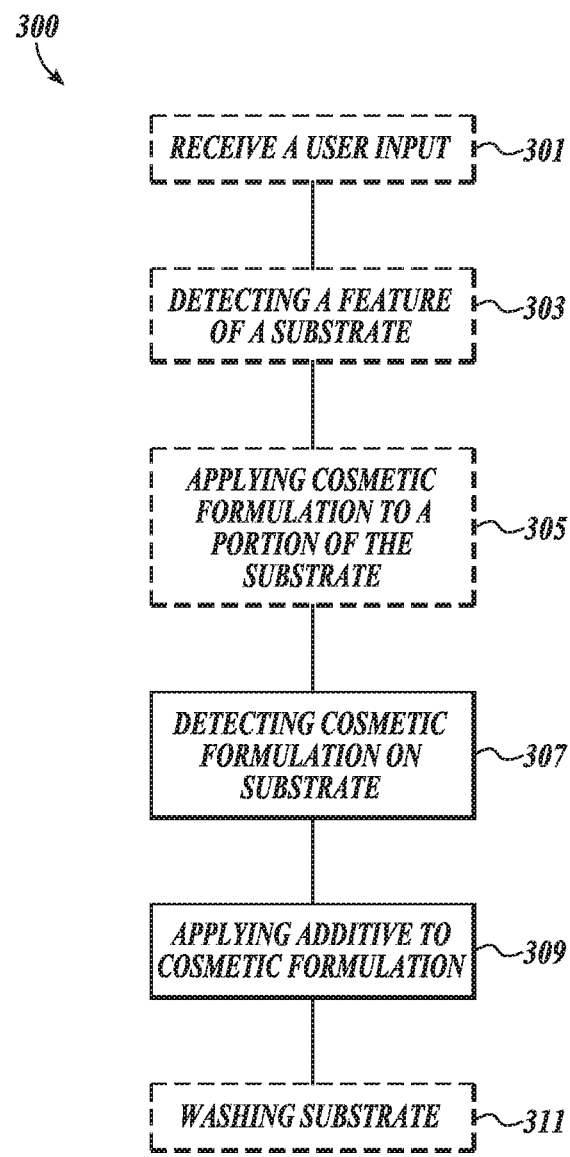
FIG. 3 is a block diagram of a method of changing an attribute of a cosmetic formulation disposed on a substrate, in accordance with an embodiment of the disclosure.

In another aspect, the present disclosure provides a method of changing an attribute of a cosmetic formulation. Accordingly, a method of changing an attribute of a cosmetic formulation, in accordance with an embodiment of the disclosure, will now be described with reference to FIG. 3. FIG. 3 is a block diagram of a method of changing an attribute of a cosmetic formulation disposed on a substrate, in accordance with an embodiment of the disclosure. In an embodiment, the method may be used to operate systems 100 and/or 200.

As shown the method can begin with process block 301, which includes receiving a user input. As discussed further herein with respect to FIG. 2C, receiving a user input can include receiving, from a user input, a signal based upon an input from a user. In an embodiment, such signals are based upon a cosmetic formulation attribute or cosmetic formulation attribute design selected by a user, such as selected with the user input. In an embodiment, the input from the user relates to where an additive is applied, how much of an additive is applied, a cosmetic formulation attribute, such as a texture, reflectance, and the like, of a cosmetic formulation, where an additive is not applied, and the like. In an embodiment, the input from the user relates to whether, where, or what type of a cosmetic formulation is applied to a substrate. As discussed above, such user input can be used to determine application of a cosmetic formulation and an additive applied thereto. In an embodiment, process block 301 is optional.

In an embodiment, process block 301 is followed by process block 303, which includes detecting a feature of a substrate. In an embodiment detecting a feature of a substrate include detecting with a detector, such as detectors 104 and 204, a feature of a substrate. Detecting the feature can include detecting a position of a feature relative to other aspects or features of the substrate, detecting a periphery or topography of the feature on the substrate, and the like. In an embodiment, the feature is detected based upon a selection made in process block 301, such as where a user input designates a feature of the substrate, such as wrinkles, lips, or the like, to be detected. In an embodiment, process block 303 is optional.

In an embodiment, process blocks 301 and 303 can be followed by process block 305, which includes applying a cosmetic formulation to the substrate. In an embodiment, applying the cosmetic formulation to the substrate includes applying the cosmetic formulation to the substrate with a formulation applicator, such as a formulation applicator 224 of system 200. In an embodiment, applying the cosmetic formulation to the substrate is based upon a detected feature of the substrate, such as a detected feature from process block 303. In this regard, in an embodiment, the cosmetic formulation is applied to a portion of the substrate, for example, including the feature. In an embodiment, applying the cosmetic formulation to the substrate is based upon an input from a user. In this regard, in an example, the cosmetic formulation is applied to the substrate based upon a desired cosmetic formulation attribute or to a selected feature of the substrate. In an embodiment, process block 305 is optional.

In an embodiment, process blocks 301, 303, or 305 are followed by process block 307, which includes detecting, with a detector, the cosmetic formulation disposed on the substrate. In an embodiment, detecting the cosmetic formulation disposed on the substrate include detecting the cosmetic formulation with a detector, such as detector 104 or detector 204. In an embodiment, detection includes optical detection, such as detecting with a detector electromagnetic radiation reflected, scattered, absorbed, emitted, and the like from or by the cosmetic formulation disposed on the substrate. Such detection can include detecting a position or an amount of the cosmetic formulation disposed on the substrate.

In an embodiment, process block 307 is followed by process block 309, which includes applying an additive to the cosmetic formulation disposed on the surface. In an embodiment, applying the additive to the cosmetic formulation includes applying, with an additive applicator, such as additive applicators 112 or 212, the additive to the formulation disposed on the substrate.

As discussed further herein, the additive is configured to change a cosmetic formulation attribute of the cosmetic formulation. As discussed with respect to FIGS. 1A-1C, in an embodiment, the cosmetic formulation comprises a polymer and applying the additive crosslinks the polymer, thereby contracting the formulation. Such contraction may be suitable, for example, to reduce the size or number of wrinkles on a portion of skin. In an embodiment, the additive includes an additive selected from the group consisting of electromagnetic radiation, heat, a plasma, and combinations thereof. In an embodiment, the cosmetic formulation includes a water-swellable polymer; and applying the additive includes applying water to the water-swellable polymer, thereby expanding the cosmetic formulation. Such expansion can be suitable, for example, to swell or plump a facial feature, such as lips.

As discussed further herein with respect to FIGS. 2A-2C, in an embodiment, application of the additive to the substrate is based on input from a user, such as input received from a user input, such as from process block 301, defining a cosmetic formulation attribute design. In an embodiment, application of the additive to the substrate is based upon a detected feature of the substrate, such as a feature detected in process block 303.

In an embodiment, process block 309 is followed by process block 311, which includes washing the substrate. Such washing can include removing cosmetic formulation that was not contacted by or reacted with the additive. For example, where the additive crosslinks or otherwise fixes or cures the cosmetic formulation, cosmetic formulation that was not contacted by the additive may be removed, such as by selectively washing, agitating, and the like the cosmetic formulation that was not contacted by the additive. In an embodiment, washing the substrate is based upon a user input, such as a user input received in process block 301, as part of a cosmetic formulation attribute design. In this regard, a component of the cosmetic formulation attribute design can include a designation of where cosmetic formulation should and should not be on the substrate.

The order in which some or all of the process blocks appear in each process should not be deemed limiting. Rather, one of ordinary skill in the art having the benefit of the present disclosure will understand that some of the process blocks may be executed in a variety of orders not illustrated, or even in parallel.

In another aspect, the present disclosure provides non-transitory machine-readable storage medium having instructions stored thereon, which when executed by a processing system, cause a processing system to perform a method, in accordance with an embodiment of the disclosure, such as described further herein with respect to FIG. 3. Accordingly, in an embodiment, the non-transitory, machine-readable storage medium includes instructions stored thereon, which when executed by a processing system, cause the processing system to perform a method comprising detecting, with a detector, the cosmetic formulation disposed on the substrate; and applying, with an additive applicator, the additive to the cosmetic formulation disposed on the substrate to change the cosmetic formulation attribute of the cosmetic formulation.

Certain embodiments disclosed herein utilize circuitry in order to implement treatment protocols, operably couple two or more components, generate information, determine operation conditions, control an appliance or method, process signals, and/or the like. Circuitry of any type can be used. In an embodiment, circuitry includes, among other things, one or more computing devices such as a processor (e.g., a microprocessor), a central processing unit (CPU), a digital signal processor (DSP), an application-specific integrated circuit (ASIC), a field-programmable gate array (FPGA), or the like, or any combinations thereof, and can include discrete digital or analog circuit elements or electronics, or combinations thereof. In an embodiment, circuitry includes one or more ASICs having a plurality of predefined logic components. In an embodiment, circuitry includes one or more FPGA having a plurality of programmable logic components.

In an embodiment, circuitry includes hardware circuit implementations (e.g., implementations in analog circuitry, implementations in digital circuitry, and the like, and combinations thereof). In an embodiment, circuitry includes combinations of circuits and computer program products having software or firmware instructions stored on one or more computer readable memories that work together to cause a device to perform one or more methodologies or technologies described herein. In an embodiment, circuitry includes circuits, such as, for example, microprocessors or portions of microprocessor, that require software, firmware, and the like for operation. In an embodiment, circuitry includes an implementation comprising one or more processors or portions thereof and accompanying software, firmware, hardware, and the like. In an embodiment, circuitry includes a baseband integrated circuit or applications processor integrated circuit or a similar integrated circuit in a server, a cellular network device, other network device, or other computing device. In an embodiment, circuitry includes one or more remotely located components. In an embodiment, remotely located components are operably coupled via wireless communication. In an embodiment, remotely located components are operably coupled via one or more receivers, transmitters, transceivers, or the like.

In an embodiment, circuitry includes one or more memory devices that, for example, store instructions or data. Non-limiting examples of one or more memory devices include volatile memory (e.g., Random Access Memory (RAM), Dynamic Random Access Memory (DRAM), or the like), non-volatile memory (e.g., Read-Only Memory (ROM), Electrically Erasable Programmable Read-Only Memory (EEPROM), Compact Disc Read-Only Memory (CD-ROM), or the like), persistent memory, or the like. Further non-limiting examples of one or more memory devices include Erasable Programmable Read-Only Memory (EPROM), flash memory, or the like. The one or more memory devices can be coupled to, for example, one or more computing devices by one or more instructions, data, or power buses.

In an embodiment, circuitry of the systems 100 or 200 include a computer-readable media drive or memory slot configured to accept signal-bearing medium (e.g., computer-readable memory media, computer-readable recording media, or the like). In an embodiment, a program for causing a system to execute any of the disclosed methods can be stored on, for example, a computer-readable recording medium (CRMM), a signal-bearing medium, or the like.

Non-limiting examples of signal-bearing media include a recordable type medium such as any form of flash memory, magnetic tape, floppy disk, a hard disk drive, a Compact Disc (CD), a Digital Video Disk (DVD), Blu-Ray Disc, a digital tape, a computer memory, or the like, as well as transmission type medium such as a digital and/or an analog communication medium (e.g., a fiber optic cable, a waveguide, a wired communications link, a wireless communication link (e.g., transmitter, receiver, transceiver, transmission logic, reception logic, etc.). Further non-limiting examples of signal-bearing media include, but are not limited to, DVD-ROM, DVD-RAM, DVD+RW, DVD-RW, DVD-R, DVD+R, CD-ROM, Super Audio CD, CD-R, CD+R, CD+RW, CD-RW, Video Compact Discs, Super Video Discs, flash memory, magnetic tape, magneto-optic disk, MINIDISC, non-volatile memory card, EEPROM, optical disk, optical storage, RAM, ROM, system memory, web server, or the like.

It should be noted that for purposes of this disclosure, terminology such as "upper," "lower," "vertical," "horizontal," "inwardly," "outwardly," "inner," "outer," "front," "rear," etc., should be construed as descriptive and not limiting the scope of the claimed subject matter. Further, the use of "including," "comprising," or "having" and variations thereof herein is meant to encompass the items listed thereafter and equivalents thereof as well as additional items. Unless limited otherwise, the terms "connected," "coupled," and "mounted" and variations thereof herein are used broadly and encompass direct and indirect connections, couplings, and mountings. In some embodiments, the term "about" means plus or minus 5% of the stated value.

The principles, representative embodiments, and modes of operation of the present disclosure have been described in the foregoing description. However, aspects of the present disclosure which are intended to be protected are not to be construed as limited to the particular embodiments disclosed. Further, the embodiments described herein are to be regarded as illustrative rather than restrictive. It will be appreciated that variations and changes may be made by others, and equivalents employed, without departing from the spirit of the present disclosure. Accordingly, it is expressly intended that all such variations, changes, and equivalents fall within the spirit and scope of the present disclosure, as claimed.

While illustrative embodiments have been illustrated and described, it will be appreciated that various changes can be made therein without departing from the spirit and scope of the claimed subject matter.

The enbodiments of the invention in which an exclusive property or privilege is claimed are defined as follows:

1. A system for changing a cosmetic formulation attribute of a cosmetic formulation disposed on a substrate, the system comprising:
 a cosmetic formulation, wherein the cosmetic formulation includes a polymer configured to crosslink upon exposure to an additive;
 a cosmetic formulation applicator configured to apply the cosmetic formulation to at least a portion of the substrate;
 a detector configured to detect the cosmetic formulation disposed on the substrate;
 an additive applicator configured to apply the additive to the cosmetic formulation disposed on the substrate, wherein the additive is configured to change a cosmetic formulation attribute; and
 a controller operatively coupled to the detector, the cosmetic formulation applicator, and the additive applicator, wherein the controller includes logic that, when executed by the controller, is configured to cause the system to perform operations including:
  selectively applying, with the cosmetic applicator, the cosmetic formulation to the substrate based upon the cosmetic formulation attribute;
  detecting, with the detector, the cosmetic formulation disposed on the substrate; and
  selectively applying, with the additive applicator, the additive to the cosmetic formulation disposed on the substrate to change the cosmetic formulation attribute of the cosmetic formulation, thereby contracting the cosmetic formulation.

2. The system of claim 1, wherein the additive includes electromagnetic radiation, wherein the additive applicator includes a light source configured to apply the electromagnetic radiation to the cosmetic formulation disposed on the substrate, and wherein the operations further include applying, with the additive applicator, the electromagnetic radiation to the cosmetic formulation for a duration and at an intensity sufficient to crosslink the polymer in the cosmetic formulation.

3. The system of claim 1, wherein the polymer is a component of a thermoset configured to crosslink upon exposure to heat, and wherein the additive applicator is configured to apply heat to the cosmetic formulation disposed on the substrate for a time and at a temperature sufficient to crosslink the thermoset.

4. The system of claim 1, wherein the additive applicator is configured to generate a plasma and apply the plasma to the cosmetic formulation disposed on the substrate, and wherein the polymer is configured to crosslink upon exposure to the plasma.

5. The system of claim 1, wherein the additive applicator is configured to apply an additive selected from a crosslinker and an initiator to the cosmetic formulation disposed on the substrate, and wherein, prior to application of the additive, the cosmetic formulation does not include a crosslinking component selected from a crosslinker and an initiator.

6. A system for changing a cosmetic formulation attribute of a cosmetic formulation disposed on a substrate, the system comprising:
 a cosmetic formulation, wherein the cosmetic formulation includes a water-swellable polymer configured to expand upon exposure to water;
 a cosmetic formulation applicator configured to apply the cosmetic formulation to at least a portion of the substrate;
 a detector configured to detect the cosmetic formulation disposed on the substrate;
 an additive applicator configured to apply water to the cosmetic formulation disposed on the substrate, thereby swelling the cosmetic formulation; and
 a controller operatively coupled to the detector, the cosmetic formulation applicator and the additive applicator, wherein the controller includes logic that, when executed by the controller, is configured to cause the system to perform operations including:
  selectively applying, with the cosmetic applicator, the cosmetic formulation to the substrate based upon the cosmetic formulation attribute;
  detecting, with the detector, the cosmetic formulation disposed on the substrate; and
  selectively applying, with the additive applicator, water to the cosmetic formulation disposed on the substrate to change the cosmetic formulation attribute of the cosmetic formulation.

7. The system of claim 1, further comprising a user input configured to receive input from a user to define, at least in part, the cosmetic formulation attribute.

8. The system of claim 7, wherein the user input is operatively coupled to the controller, and wherein the controller further includes logic that, when executed by the controller, is configured to cause the system to perform operations including:

applying the additive to at least a portion of the cosmetic formulation disposed on the substrate based upon the cosmetic formulation attribute.

9. The system of claim 7, wherein the controller further includes logic that, when executed by the controller, is configured to cause the system to perform operations including:

detecting, with the detector, a feature of the substrate; and
applying the additive to at least a portion of the cosmetic formulation disposed on the substrate based upon the cosmetic formulation attribute and the feature of the substrate.

10. The system of claim 1, wherein the substrate is chosen from a finger nail, skin, hair, and combinations thereof.

11. The system of claim 1, wherein the cosmetic formulation is chosen from a lotion, a hair dye, a foundation, a blush, a rouge, a lipstick, a lip gloss, a nail polish, and a nail varnish.

12. A method of changing an attribute of a cosmetic formulation disposed on a substrate, the method comprising:

applying, with a cosmetic formulation applicator, the cosmetic formulation to the substrate based upon a cosmetic formulation attribute, wherein the cosmetic formulation includes a polymer configured to crosslink upon exposure to an additive, thereby contracting the cosmetic formulation;

detecting, with a detector, the cosmetic formulation disposed on the substrate; and
applying, with an additive applicator, the additive to the cosmetic formulation disposed on the substrate to change the cosmetic formulation attribute of the cosmetic formulation.

13. The system of claim 6, further comprising a user input configured to receive input from a user to define, at least in part, the cosmetic formulation attribute.

14. The system of claim 13, wherein the user input is operatively coupled to the controller, and wherein the controller further includes logic that, when executed by the controller, is configured to cause the system to perform operations including:

applying water to at least a portion of the cosmetic formulation disposed on the substrate based upon the cosmetic formulation attribute.

15. The system of claim 13, wherein the controller further includes logic that, when executed by the controller, is configured to cause the system to perform operations including:

detecting, with the detector, a feature of the substrate; and
applying water to at least a portion of the cosmetic formulation disposed on the substrate based upon the cosmetic formulation attribute and the feature of the substrate.

16. The system of claim 6, wherein the substrate is chosen from a finger nail, skin, hair, and combinations thereof.

17. The system of claim 6, wherein the cosmetic formulation is chosen from a lotion, a hair dye, a foundation, a blush, a rouge, a lipstick, a lip gloss, a nail polish, and a nail varnish.

* * * * *